United States Patent
Aslan et al.

(10) Patent No.: US 11,497,700 B2
(45) Date of Patent: Nov. 15, 2022

(54) HAIR TREATMENT COMPOSITION

(71) Applicant: L'OREAL, Paris (FR)

(72) Inventors: Seyma Aslan, Clifton, NJ (US); Rita Chokshi, Monroe Township, NJ (US)

(73) Assignee: L'OREAL, Paris (FR)

( * ) Notice: Subject to any disclaimer, the term of this patent is extended or adjusted under 35 U.S.C. 154(b) by 28 days.

(21) Appl. No.: 17/035,894

(22) Filed: Sep. 29, 2020

(65) Prior Publication Data

US 2021/0093542 A1  Apr. 1, 2021

Related U.S. Application Data

(60) Provisional application No. 62/908,159, filed on Sep. 30, 2019.

(51) Int. Cl.
| | |
|---|---|
| *A61Q 5/12* | (2006.01) |
| *A61K 8/73* | (2006.01) |
| *A61K 8/34* | (2006.01) |
| *A61K 8/365* | (2006.01) |
| *A61K 8/41* | (2006.01) |
| *A61K 8/81* | (2006.01) |
| *A61K 8/898* | (2006.01) |

(52) U.S. Cl.
CPC ............ *A61K 8/731* (2013.01); *A61K 8/342* (2013.01); *A61K 8/345* (2013.01); *A61K 8/365* (2013.01); *A61K 8/416* (2013.01); *A61K 8/8158* (2013.01); *A61K 8/898* (2013.01); *A61Q 5/12* (2013.01); *A61K 2800/5426* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 2003/0049221 A1 | 3/2003 | Cannell et al. | |
| 2004/0221401 A1 | 11/2004 | Desenne et al. | |
| 2004/0234489 A1 | 11/2004 | Muller | |
| 2005/0011017 A1 | 1/2005 | Legrand et al. | |
| 2005/0129644 A1 | 6/2005 | Sabbagh et al. | |
| 2007/0226916 A1 | 10/2007 | Mellul et al. | |
| 2007/0297999 A1 | 12/2007 | Fonolla Moreno et al. | |
| 2008/0051461 A1 | 2/2008 | Aubrun-Sonneville et al. | |
| 2008/0292577 A1 | 11/2008 | Mougin et al. | |
| 2008/0311066 A1 | 12/2008 | Samain et al. | |
| 2009/0029928 A1 | 1/2009 | Aubrun-Sonneville | |
| 2009/0035294 A1 | 2/2009 | Mahe et al. | |
| 2010/0009931 A1 | 1/2010 | Laboureau et al. | |
| 2012/0070399 A1 | 3/2012 | Jegou | |
| 2012/0199154 A1 * | 8/2012 | Schweinsberg | A61K 8/88 132/203 |
| 2013/0139844 A1 | 6/2013 | Malle et al. | |
| 2013/0233331 A1 | 9/2013 | Khenniche et al. | |
| 2013/0233332 A1 | 9/2013 | Khenniche et al. | |
| 2013/0251656 A1 | 9/2013 | Khenniche et al. | |
| 2013/0266529 A1 | 10/2013 | Deconinck et al. | |
| 2016/0193133 A1 | 7/2016 | Biato | |
| 2017/0151142 A1 * | 6/2017 | Scheunemann | A61K 8/23 |
| 2018/0055751 A1 | 3/2018 | Gevgilili et al. | |
| 2019/0029949 A1 | 1/2019 | Ceballos et al. | |
| 2019/0060195 A1 | 2/2019 | Elsen et al. | |
| 2019/0060196 A1 | 2/2019 | Elsen et al. | |
| 2020/0179257 A1 | 6/2020 | Gevgilili et al. | |

FOREIGN PATENT DOCUMENTS

| | | | | |
|---|---|---|---|---|
| FR | 2864775 A1 * | 7/2005 | ............ | A61K 8/20 |
| WO | WO-2012112019 A1 * | 8/2012 | ............ | C02F 1/4674 |
| WO | 2016/172158 A1 | 10/2016 | | |
| WO | 2019/095152 A1 | 5/2019 | | |

OTHER PUBLICATIONS

International Search Report and Written Opinion dated Dec. 21, 2020 for corresponding PCT Application No. PCT/US2020/053187.

* cited by examiner

*Primary Examiner* — Jyothsna A Venkat
(74) *Attorney, Agent, or Firm* — Polsinelli PC

(57) ABSTRACT

Hair treatment compositions containing about 0.1 to about 8 wt. % of xylan or derivatives thereof; about 0.2 to about 23 wt. % of gluconic acid; about 2 to about 45 wt. % of sorbitol; and water, wherein all percentages by weight are based on the total weight of the cosmetic composition. The weight fraction of the total amount of xylan or derivatives thereof to the total amount of gluconic acid is greater than 0.2 to less than 1. Example hair treatment compositions may form a film of xylan or derivatives thereof and gluconic acid on an individual's hair after the hair treatment composition has been rinsed from the hair. Methods for producing and using such hair treatment compositions are also provided.

6 Claims, 4 Drawing Sheets

HAIR TREATMENT COMPOSITION

CROSS-REFERENCE TO RELATED APPLICATIONS

This application claims benefit of U.S. Provisional Application No. 62/908,159, filed Sep. 30, 2019, which is incorporated herein by reference in its entirety.

FIELD OF THE DISCLOSURE

The instant disclosure is directed to hair treatment compositions having a xylan or derivatives thereof, gluconic acid, and sorbitol, as well as concentrates thereof. Methods for producing and using such hair treatment compositions are also disclosed herein.

BACKGROUND OF THE DISCLOSURE

Many individuals suffer from dry and damaged hair. Dryness and damage can occur due to several factors including weather exposure, mechanical treatments (e.g. brushing hair), excessive treatments using chemicals, dying hair, heat styling, etc. In addition, using cleansing products that can be excessively stripping of hair's natural oils or products for controlling frizzy hair can also lead to split ends, dull hair, and exacerbate dry hair. To mitigate the damage, many individuals utilize conditioners or other hair treatments for mitigating the damage and improve the health of hair.

Presently available conditioners, however, provided limited and often insufficient frizz control, smoothness, and closure of the ends. Additionally, conventional conditioners often fail to provide long lasting conditioning effects.

There is an ongoing need for improved conditioners and hair treatment products that provide conditioning effects, frizz control, improved smoothness, and enhanced closure of the ends.

SUMMARY OF THE DISCLOSURE

The instant disclosure is directed to hair treatment compositions having a xylan or derivatives thereof, gluconic acid, and sorbitol, as well as concentrates thereof. Methods for producing and using such hair treatment compositions are also disclosed herein. Exemplary hair treatment compositions may form a film of xylan or derivatives thereof and gluconic acid (also referred herein as a xylan-gluconic acid film) on an individual's hair after the hair treatment composition has been rinsed from the hair. The xylan-gluconic acid film enables the hair treatment compositions to provide enhanced smoothness, frizz-control, alignment, and closure of the ends. Additionally, the xylan-gluconic film may have a unique texture that provides a desirable tactile sensation.

According to at least one theory, but not bound by such theory, the xylan-gluconic acid film may have a structure having a backbone formed of xylan compounds or derivatives thereof substituted with gluconic acid. In at least one instance, the xylan-gluconic acid film has a crystalline network.

The hair treatment composition typically includes:
  (a) about 0.1 to about 8 wt. % of xylan or derivatives thereof;
  (b) about 0.2 to about 23 wt. % of gluconic acid,
     wherein a weight fraction of the total amount of xylan or derivatives thereof to the total amount of gluconic acid is greater than 0.2 to less than 1,
  (c) about 2 to about 45 wt. % of sorbitol; and
  (d) water,
     wherein all percentages by weight are based on the total weight of the hair treatment composition.

The hair treatment composition may have about 0.1 to about 3 wt. % of xylan or derivatives thereof; about 0.2 to about 8 wt. % of gluconic acid; and about 3.5 to about 25 wt. % of sorbitol. The hair treatment composition may be in a more diluted form and having about 0.1 to about 1 wt. % of xylan or derivatives thereof; about 0.2 to about 2 wt. % of gluconic acid; and about 3.5 to about 5 wt. % of sorbitol. The weight fraction of the total amount of xylan or derivatives thereof to the total amount of gluconic acid may be from 0.25 to 0.75, and in some instances from 0.3 to 0.7.

In some instances, the hair treatment composition further includes about 1% to about 10 wt. % of one or more silicone. The silicones may be an amino functionalized silicone. The amino functionalized silicone may be chosen from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof.

Additionally or alternatively, the hair treatment composition may include about 0.1% to about 10 wt. % of one or more cationic surfactant. The cationic surfactant may be chosen from behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and a mixture thereof.

The hair treatment composition may also have about 2 to about 20 wt. % of one or more fatty compounds. In some instances, the one or more the fatty compounds is from one or more fatty alcohols having a carbon chain of 12 to 22 carbon atoms. In at least one instance, the fatty alcohol includes or is chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis-4-t-butylcyclohexanol, isotridecyl alcohol, myricyl alcohol, and a mixture thereof.

The hair treatment composition may include one or more cationic polymers. The one or more cationic polymers may include or be chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium- 53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

The hair treatment compositions may be a conditioner. The instant disclosure also relates to methods for treating hair. The hair treatment composition may be used in a method for improving smoothness, frizz-control, and alignment by applying the hair treatment composition to hair. The method may also include rinsing the hair treatment composition from the hair.

BRIEF DESCRIPTION OF THE DRAWING

Implementation of the present technology will now be described, by way of example only, with reference to the attached figures, wherein.

Figure 1:
FIG. 1 includes images of hair after applying a hair treatment composition according to aspects of the disclosure to half an individual's head and a comparative composition to the other half of the individual's head.

It should be understood that the various aspects are not limited to the arrangements and instrumentality shown in the drawings.

DETAILED DESCRIPTION OF THE DISCLOSURE

The instant disclosure is directed to hair treatment compositions having xylan or derivatives thereof, gluconic acid, and sorbitol, as well as concentrates thereof. The hair treatment compositions, preferably, form a xylan-gluconic acid film that remains on the hair of an individual, e.g., after rinsing the hair treatment composition from the hair, for at least 2 hours, preferably at least 4 hours, preferably at least 8 hours, preferably at least 16 hours, preferably at least 24 hours, or preferably at least 48 hours. The hair treatment compositions and/or the xylan-gluconic acid film formed therefrom may provide enhanced smoothness, frizz-control, alignment, and closure of the ends.

The hair treatment composition typically includes:
(a) about 0.1 to about 8 wt. % of xylan or derivatives thereof;
(b) about 0.2 to about 23 wt. % of gluconic acid,
  wherein a weight fraction of the total amount of xylan or derivatives thereof to the total amount of gluconic acid is greater than 0.2 to less than 1,
(c) about 2 to about 45 wt. % of sorbitol; and
(d) water,
  wherein all percentages by weight are based on the total weight of the hair treatment composition.

As mentioned above, the xylan-gluconic acid film may have a structure formed of xylan compounds or derivatives thereof substituted with gluconic acid. In at least one instance, the xylan-gluconic acid film consists essentially of or consists of xylan (and/or derivatives thereof) and gluconic acid. For example, the xylan-gluconic acid film may be formed of less than 10 wt. %, preferably less than 9 wt. %, preferably less than 8 wt. %, preferably less than 7 wt. %, preferably less than 6 wt. %, preferably less than 5 wt. %, preferably less than 4 wt. %, preferably less than 3 wt. %, preferably less than 2 wt. %, or preferably less than 1 wt. % of components/compounds other than xylan and/or derivatives thereof and gluconic acid. The xylan-gluconic film may have a unique texture that provides a desirable tactile sensation. Methods for producing and using such hair treatment compositions are also disclosed herein.

Suitable components, such as those listed below, may be included in or excluded from the hair treatment compositions, depending on the specific combination of other components, the form of the hair treatment compositions, and/or the use of the formulation.

Xylan

The hair treatment composition includes xylan or derivatives thereof typically in the amount of about 0.01 to about 8 wt. %, based on the total weight of the hair treatment composition. For example, the hair treatment composition may include about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %, about 0.1 to about 0.3 wt. %; about 0.15 to about 8 wt. %, about 0.15 to about 7 wt. %, about 0.15 to about 6 wt. %, about 0.15 to about 5 wt. %, about 0.15 to about 4 wt. %, about 0.15 to about 3 wt. %, about 0.15 to about 2 wt. %, about 0.15 to about 1 wt. %, about 0.15 to about 0.5 wt. %, or about 0.15 to about 0.3 wt. %, including all ranges and sub-ranges therebetween, based on the total weight of the hair treatment composition.

In some instances, the hair treatment composition may formulated, e.g., as a concentrate, with higher amounts of xylan or derivatives thereof. For example, the hair treatment composition may have an amount of xylan or derivatives thereof present of about 0.2 to about 8 wt. %, about 0.2 to about 7 wt. %, about 0.2 to about 6 wt. %, about 0.2 to about 5 wt. %, about 0.2 to about 4 wt. %, about 0.2 to about 3 wt. %, about 0.2 to about 2 wt. %, about 0.2 to about 1 wt. %; about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 8 wt. %, about 2 to about 7 wt. %, about 2 to about 6 wt. %, about 2 to about 5 wt. %, about 2 to about 4 wt. %, about 2 to about 3 wt. %, about 3 to about 8 wt. %, about 3 to about 7 wt. %, about 3 to about 6 wt. %, about 3 to about 5 wt. %, or about 3 to about 4 wt. %, including all ranges and sub-ranges therebetween, based on the total weight of the hair treatment composition.

Gluconic Acid

The hair treatment composition includes gluconic acid typically in the amount of about 0.2 to about 23 wt. %, based on the total weight of the hair treatment composition. For example, the hair treatment may include about 0.2 to about 23 wt. %, about 0.2 to about 20 wt. %, about 0.2 to about 15 wt. %, about 0.2 to about 10 wt. %, about 0.2 to about 8 wt. %, about 0.2 to about 6 wt. %, about 0.2 to about 4 wt. %, about 0.2 to about 3 wt. %, about 0.2 to about 2 wt. %, about 0.2 to about 1 wt. %, including all ranges and sub-ranges therebetween, based on the total weight of the hair treatment composition.

In some instances, the hair treatment composition may formulated, e.g., as a concentrate, with higher amounts of gluconic acid. For example, the hair treatment composition may have an amount of gluconic acid present of about 0.35 to about 23 wt. %, about 0.35 to about 20 wt. %, about 0.35 to about 15 wt. %, about 0.35 to about 10 wt. %, about 0.35 to about 8 wt. %, about 0.35 to about 6 wt. %, about 0.35 to about 4 wt. %, about 0.35 to about 3 wt. %, about 0.35 to about 2 wt. %, about 0.35 to about 1 wt. %; about 0.5 to about 23 wt. %, about 0.5 to about 20 wt. %, about 0.5 to about 15 wt. %, about 0.5 to about 10 wt. %, about 0.5 to about 8 wt. %, about 0.5 to about 6 wt. %, about 0.5 to about 4 wt. %, about 0.5 to about 3 wt. %, about 0.5 to about 2 wt. %, or about 0.5 to about 1 wt. %; about 1 to about 23 wt. %, about 1 to about 20 wt. %, about 1 to about 15 wt. %, about 1 to about 10 wt. %, about 1 to about 8 wt. %, about 1 to about 6 wt. %, about 1 to about 4 wt. %, about 1 to about 3 wt. %, about 1 to about 2 wt. %; about 2 to about 23 wt. %, about 2 to about 20 wt. %, about 2 to about 15 wt. %, about 2 to about 10 wt. %, about 2 to about 8 wt. %, about 2 to about 6 wt. %, about 2 to about 4 wt. %, about 2 to about 3 wt. %; about 5 to about 23 wt. %, about 5 to about 20 wt. %, about 5 to about 15 wt. %, about 5 to about 10 wt. %, about 5 to about 8 wt. %, about 5 to about 6 wt. %; about 8 to about 23 wt. %, about 8 to about 20 wt. %, about 8 to about 15 wt. %, about 8 to about 10 wt. %, including all ranges and sub-ranges therebetween, based on the total weight of the hair treatment composition.

Sorbitol (Hydrogenated Starch Hydrolysate)

The hair treatment composition includes sorbitol typically in the amount of about 2 to about 45 wt. %, based on the total weight of the hair treatment composition. For example, the hair treatment may include about 2 to about 45 wt. %, about 2 to about 42 wt. %, about 2 to about 40 wt. %, about 2 to about 40 wt. %, about 2 to about 35 wt. %, about 2 to about 30 wt. %, about 2 to about 25 wt. %, about 2 to about 20 wt. %, about 2 to about 15 wt. %, about 2 to about 10 wt. %, about 2 to about 9 wt. %, about 2 to about 8 wt. %, about 2 to about 7 wt. %, about 2 to about 6 wt. %, about 2 to about 5 wt. %; 2.5 to about 45 wt. %, about 2.5 to about 42 wt. %, about 2.5 to about 40 wt. %, about 2.5 to about 40 wt. %, about 2.5 to about 35 wt. %, about 2.5 to about 30 wt. %, about 2.5 to about 25 wt. %, about 2.5 to about 20 wt. %, about 2.5 to about 15 wt. %, about 2.5 to about 10 wt. %, about 2.5 to about 9 wt. %, about 2.5 to about 8 wt. %, about 2.5 to about 7 wt. %, about 2.5 to about 6 wt. %, about 2.5 to about 5 wt. %; 3 to about 45 wt. %, about 3 to about 42 wt. %, about 3 to about 40 wt. %, about 3 to about 40 wt. %, about 3 to about 35 wt. %, about 3 to about 30 wt. %, about 3 to about 25 wt. %, about 3 to about 20 wt. %, about 3 to about 15 wt. %, about 3 to about 10 wt. %, about 3 to about 9 wt. %, about 3 to about 8 wt. %, about 3 to about 7 wt. %, about 3 to about 6 wt. %, about 3 to about 5 wt. %; 3.5 to about 45 wt. %, about 3.5 to about 40 wt. %, about 3.5 to about 35 wt. %, about 3.5 to about 30 wt. %, about 3.5 to about 25 wt. %, about 3.5 to about 20 wt. %, about 3.5 to about 15 wt. %, about 3.5 to about 10 wt. %, about 3.5 to about 9 wt. %, about 3.5 to about 8 wt. %, about 3.5 to about 7 wt. %, about 3.5 to about 6 wt. %, about 3.5 to about 5 wt. %, including all ranges and sub-ranges therebetween, based on the total weight of the hair treatment composition.

In some instances, the hair treatment composition may formulated, e.g., as a concentrate, with higher amounts of sorbitol. For example, the hair treatment composition may have an amount of sorbitol present of about 5 to about 45 wt. %, about 5 to about 40 wt. %, about 5 to about 35 wt. %, about 5 to about 30 wt. %, about 5 to about 25 wt. %, about 5 to about 20 wt. %, about 5 to about 15 wt. %, about 5 to about 10 wt. %, about 5 to about 9 wt. %, about 5 to about 8 wt. %, about 5 to about 7 wt. %; about 5 to about 45 wt. %, about 5 to about 40 wt. %, about 5 to about 35 wt. %, about 5 to about 30 wt. %, about 5 to about 25 wt. %, about 5 to about 20 wt. %, about 5 to about 15 wt. %, about 5 to about 10 wt. %, about 5 to about 9 wt. %, about 5 to about 8 wt. %, or about 5 to about 7 wt. %, including all ranges and sub-ranges therebetween, based on the total weight of the hair treatment composition.

The amount of sorbitol present in the hair treatment composition may due to the inclusion of hydrogenated starch hydrolysate in the hair treatment composition. Hydrogenated starch hydrolysate are mixtures of sugar alcohols, including sorbitol, maltitol, maltotriitol and other hydrogenated oligosaccharides and polysaccharides. The hair treatment composition may include an amount of hydrogenated starch hydrolysate, such that the hair treatment composition includes any of the amounts of sorbitol listed above.

Silicone(s)

The hair treatment compositions may include one or more silicones. The total amount of the one or more silicones can vary but is typically from about 0.1 to about 15 wt. %, based on the total weight of the hair-treatment composition. The total amount of the silicones may be from about 0.1 to about 15 wt. %, about 0.1 to about 12 wt. %, about 0.1 to about 10 wt. %, about 0.1 to about 8 wt. %, about 0.1 to about 6 wt. %, about 0.1 to about 5 wt. %; about 0.5 to about 15 wt. %, about 0.5 to about 12 wt. %, about 0.5 to about 10 wt. %, about 0.5 to about 8 wt. %, about 0.5 to about 6 wt. %, about 0.5 to about 5 wt. %; about 1 to about 15 wt. %, about 1 to about 12 wt. %, about 1 to about 10 wt. %, about 1 to about 8 wt. %, about 1 to about 6 wt. %, about 1 to about 5 wt. %; about 2 to about 15 wt. %, about 2 to about 12 wt. %, about 2 to about 10 wt. %, about 2 to about 8 wt. %, about 2 to about 6 wt. %, or about 2 to about 5 wt. %, including ranges and sub-ranges therebetween, based on the total weight of the hair-treatment compositions.

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

In some instances, the amino-functionalized silicones are selected from compounds of the following formula:

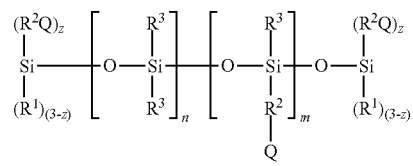

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4{}_2$ and $-NR^4(CH_2)_xNR^4{}_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

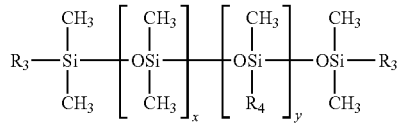

wherein $R_3$ is hydroxyl or $OR_5$; $R_5$ is a $C_1$ to $C_4$ alkyl group, $R_4$ is a group with a structure according to the following formula:

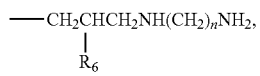

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions DC2-1766, DC2-1784, and microemulsions DC2-1865 and DC2-1870 from Dow Corning, or cross-linked silicone gums, such as DC X2-1787 or DC X2-1391 from Dow Corning.

Cationic Surfactant(s)

The hair treatment composition may optionally include one or more cationic surfactant(s) typically in an amount ranging from about 0.1 to about 10 wt. % based on the total weight of the hair treatment composition. For example, the amount of cationic surfactants present in the hair treatment composition may range from about 0.1 to about 10 wt. %, about 0.1 to about 8 wt. %, about 0.1 to about 6 wt. %, about 0.1 to about 4 wt. %, about 0.1 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including all ranges and sub-ranges therebetween, based on the total weight of the hair treatment composition.

The term "cationic surfactant" means a surfactant that may be positively charged when it is contained in the hair treatment compositions according to the disclosure. This surfactant may bear one or more positive permanent charges or may contain one or more functional groups that are cationizable in the hair treatment composition according to the disclosure.

The one or more cationic surfactants, if present, may include or be chosen from quaternary ammonium compounds, amidoamines, or a mixture thereof. Examples of cationic surfactants that may be suitable for the hair treatment composition include or may be chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include: cetyl trimethyl ammonium chloride available, for example, with trade name CA-2350 from Nikko Chemicals and CTAC 30KC available from KCl, stearyl trimethyl ammonium chloride with trade name Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Hydrophilically substituted cationic surfactants in which at least one of the substituents contain one or more aromatic, ether, ester, amido, or amino moieties present as substituents or as linkages in the chain may also be in the hair treatment composition. Non-limiting examples of hydrophilically substituted cationic surfactants that may be useful in the hair treatment compositions include the materials having the following INCI designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

In one embodiment, the hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl am idopropyl trimonium salt, polyoxyethylene alkyl ammonium salt, and mixtures thereof. For example, commercially available hydrophilically substituted cationic surfactants may include those under the following trade names; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

In certain instances, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some cases, the cationic surfactant is selected from cetrimonium chloride, behentrimonium chloride, and mixtures thereof. Non-polymeric, mono-, di-, and/or tri-carboxylic acids may be used to "neutralize" the amidoamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with amidoamines such as, for example, stearamidopropyl dimethylamine.

Fatty Compound(s)

The hair treatment compositions include one or more fatty compounds typically in an amount of about 2 to about 20 wt. %, based on the total weight of the hair treatment composition. For example, the amount of fatty compounds in the hair treatment composition may range from about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, including all ranges and sub-ranges therebetween, based on the total weight of the hair treatment composition.

Suitable fatty compounds include or may be chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof. In some instances, it may be preferable to include one or more fatty alcohols, such as those further discussed below.

Fatty Alcohols

Suitable fatty alcohols include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

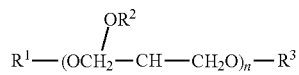

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

In some instances, the fatty compounds may include one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/ triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Cationic Polymer(s)

The hair treatment compositions may include one or more cationic polymers. The amount of cationic polymers in the hair treatment composition typically ranges from about 0.1 to about 10 wt. % of the total weight of the hair treatment composition. In some instances, the conditioning agents are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the hair treatment composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methylimidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair treatment composition may include or be chosen from polyquaterniums. For example, the hair treatment composition may include Polyquaternium-1 (ethanol, 2,2', 2"-nitrilotris-, polymer with 1,4-dichloro-2-butene and N,N, N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/ diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,Ndimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine) methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful.

In one instance, the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

Nonionic Surfactant(s)

The hair treatment compositions may, optionally, include one or more nonionic surfactants. The amount of nonionic surfactants, if present, typically range from about 0.05 to about 6 wt. % of the total weight of the hair treatment composition. For example, the total weight of the plurality of nonionic surfactants may range from about 0.05 to about 6 wt. %, 0.05 to about 5 wt. %, 0.05 to about 4 wt. %, 0.05 to about 3 wt. %; from 0.1 to about 6 wt. %, 0.1 to about 5 wt. %, 0.1 to about 4 wt. %, 0.1 to about 3 wt. %; from 0.5 to about 6 wt. %, 0.5 to about 5 wt. %, 0.5 to about 4 wt. %, 0.5 to about 3 wt. %; from 0.8 to about 6 wt. %, 0.8 to about 5 wt. %, 0.8 to about 4 wt. %, 0.8 to about 3 wt. %; from 1 to about 6 wt. %, 1 to about 5 wt. %, 1 to about 4 wt. %, or 1 to about 3 wt. %, including ranges and sub-ranges therebetween, based on the total weight of the hair treatment composition.

Examples of nonionic surfactants that may, in some cases, be suitably incorporated into the hair treatment composition include and/or may be chosen from alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

As glyceryl esters of fatty acids, glyceryl stearate (glyceryl mono-, di- and/or tristearate) (INCI name: glyceryl stearate) or glyceryl ricinoleate and mixtures thereof can be cited. As glyceryl esters of $C_8$-$C_{24}$ alkoxylated fatty acids, polyethoxylated glyceryl stearate (glyceryl mono-, di- and/ or tristearate) such as PEG-20 glyceryl stearate can for example be cited.

Additionally or alternatively, the nonionic surfactants may comprise or be selected from alkanolamides, polyglucosides, sorbitan derivatives (not including the hydration of sorbitan to derive sorbitol), and polyol esters.

Alkanolamide(s)

Non-limiting examples of alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides may include those formed by reacting an alkanolamine and a $C_6$-$C_{36}$ fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof); wherein $R_5$ is selected from —$CH_2OH$, —$CH_2CH_2OH$, —$CH_2CH_2CH_2OH$, —$CH_2(CHOH)_4$ $CH_2OH$, -benzyl, and mixtures thereof; and wherein $R_6$ is selected from —H, —$CH_3$, —$CH_2OH$, —$CH_2CH_3$, —$CH_2CH_2OH$, —$CH_2CH_2CH_2OH$, —$CH_2(CHOH)_4$ $CH_2OH$, -benzyl, and mixtures thereof.

In some instances, the one or more of the fatty acid alkanolamides include one or more acyl glucamides, e.g., acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide Alkyl Polyglucoside(s)

In some embodiments, the one or more alkyl polyglucosides include those chosen from lauryl glucoside, octyl glucoside, decyl glucoside, coco glucoside, caprylyl/capryl glucoside, sodium lauryl glucose carboxylate, and a mixture thereof. In some cases, the alkyl polyglucosides includes or is chosen from lauryl glucoside. Additionally or alternatively, the alkyl polyglucosides may be chosen from glycerol ($C_6$-$C_{24}$)alkylpolyglycosides including, e.g., polyethoxylated fatty acid mono or diesters of glycerol ($C_6$-$C_{24}$) alkylpolyglycosides. Additional alkyl polyglucosides that may be suitably incorporated, in some instances, in the hair treatment composition includes alkyl polyglucosides having a structure according to the following formula:

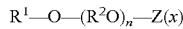

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

Sorbitan Derivative(s)

Suitable sorbitan derivatives that may be incorporated into the plurality of nonionic surfactants include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE (4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearate and a mixture thereof.

Additional and/or alternative sorbitan derivatives include sorbitan esters including, e.g., esters of $C_{16}$-$C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (INCI name: Sorbitan stearate) sold by Croda under the name Span 60, the sorbitan tristearate sold by Croda under the name Span 65 V, the sorbitan monopalmitate (INCI name: Sorbitan palmitate) sold by Croda under the name Span 40, the sorbitan monooleate sold by Croda under the name Span 80 V or the sorbitan trioleate sold by Uniqema under the name Span 85 V. A preferable sorbitan ester is sorbitan tristearate.

Polyol Ester(s)

Non-limiting examples of polyol esters include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. Additionally and/or alternatively, the polyol esters may be chosen from ethoxylated fatty acid esters of sorbitan comprising from 2 to 30 mol of ethylene oxide.

In some cases, the polyol ester may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic surfactants that may optionally be used in the hair treatment composition include and/or may be chosen from alkanolamides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Aspects of the instant disclosure are directed to kits, which include hair treatment compositions as discussed herein. For example, kits may include at least one hair treatment composition according to the instant disclosure and one or more additional compositions, such as a shampoo, a conditioner, etc. The various compositions are separately contained in the kits. In some instances, the kits include one or more hair treatment compositions according the instant disclosure, a shampoo, a conditioner, a mask, and/or other hair treatment products, all of which are separately contained.

The hair treatment compositions of the kit may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair treatment composition according to the instant disclosure, and the other tube may include a composition to be used with the hair treatment composition, for example, a shampoo, a conditioner, an all-in-one shampoo/conditioner (i.e., a conditioning shampoo; also referred to as a "co-wash") mask or other hair treatment products.

Methods of Treating Hair

Methods of treating hair according to the disclosure may vary but typically include applying a hair treatment composition as disclosed herein, allowing the hair treatment composition to remain on the hair for a sufficient amount of time, and rinsing the hair treatment compositions from the hair. The hair treatment composition may be applied to the hair in a sequence with other compositions. For example, the hair treatment composition may be applied to the hair before shampooing the hair, after shampooing the hair, before conditioning the hair, and/or after conditioning the hair, etc. The compositions, however, are not required to be used in a sequence.

The methods may include applying an amount of the hair treatment composition onto the user's hair, for example, onto one or both hands, onto the hair, etc. The user's hair may already be wet or damp with extraneous water or extraneous water can be included after the hair treatment composition has already been applied to the hair. The extraneous water typically has a temperature of about 25° to 50° C. The hair treatment composition may be applied to the user's hand(s) or directly to the hair while the user is showering and/or bathing in water having a temperature of, e.g., 25° to 50° C. The hair treatment composition may optionally be rinsed from the user's hair.

In some cases, the hair treatment compositions are used in conjunction with additional hair treatment compositions in a routine, for example, during an individual's normal showering/bathing routine. The hair treatment composition may be applied to the hair individually or may be combined with one or more additional compositions. Combining the compositions with one or more additional compositions (e.g., a shampoo, a conditioner, a rinse, etc.) can be useful for eliminating multiple steps from a routine. For instance, the hair treatment composition may be mixed with a shampoo (or conditioner) prior to application to the hair. In this case, the mixture of the shampoo (or conditioner) and the hair treatment composition are simultaneously applied to the hair during the cleansing or conditioning process and simultaneously rinsed from the hair. In at least one instance, however, the hair treatment composition is applied to hair after shampoo (or conditioner) has been rinsed from the hair. Alternatively, the hair treatment composition may be layered on top of (or lathered into) hair to which a shampoo (or conditioner) has already been applied or vice versa. For example, the hair treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair treatment composition is also applied to the hair.

When used in conjunction with a shampoo and/or a conditioner, the hair treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure: shampoo/conditioner, etc.).

The hair treatment compositions of the instant disclosure may be allowed to remain on the hair for a minimum amount of time before being rinsed from the hair, but it is not necessary to allow the hair treatment composition to remain on the hair for an extended period of time. Conveniently, the hair treatment compositions can be applied and allowed to remain on the hair for a period of time that is typical for regular shampooing and/or conditioning. For example, the hair treatment composition (whether combined with another hair treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the hair treatment composition is not being mixed with another composition prior to application to the hair, the hair treatment composition may be applied to the hair immediately after or before the hair is treated with another composition (e.g., a shampoo and/or a conditioner). For example, the hair treatment compositions may be applied to the hair within about a few seconds or 1, 2, 5, 10, or 20 minutes before or after a shampoo and/or a conditioner is applied to the hair.

EMBODIMENTS

In certain embodiments, the hair treatment compositions of the instant disclosure include:
about 0.1 to about 8 wt. %, preferably about 0.1 to about 3 wt. %, more preferably about 0.1 to about 0.3 wt. % of xylan or derivatives thereof;
about 0.2 to about 23 wt. %, preferably about 0.2 to about 8 wt. %, more preferably about 0.2 to about 1 wt. % of gluconic acid,
   wherein a weight fraction of the total amount of xylan or derivatives thereof to the total amount of gluconic acid is greater than 0.2 to less than 1, preferably greater than 0.2 and less than 0.8, more preferably about 0.25 to about 0.75, and more preferably about 0.3 to about 0.7, and even more preferably about 0.35 to about 0.6,
about 2 to about 45 wt. %, preferably about 3 to about 25 wt. %, more preferably about 3.5 to about 5 wt. %, of sorbitol; and
water, wherein all percentages by weight are based on the total weight of the cosmetic composition.

In further embodiments, the hair treatment compositions of the instant disclosure include:
about 0.1 to about 8 wt. %, preferably about 0.1 to about 3 wt. %, more preferably about 0.1 to about 0.3 wt. % of xylan or derivatives thereof;
about 0.2 to about 23 wt. %, preferably about 0.2 to about 8 wt. %, more preferably about 0.2 to about 1 wt. % of gluconic acid,
   wherein a weight fraction of the total amount of xylan or derivatives thereof to the total amount of gluconic acid greater than 0.2 to less than 1, preferably greater than 0.2 and less than 0.8, preferably about 0.25 to about 0.75, and more preferably about 0.3 to about 0.7, and even more preferably about 0.35 to about 0.6,
about 2 to about 45 wt. %, preferably about 2.5 to about 25 wt. %, more preferably about 3 to about 5 wt. %, of sorbitol; and
water, wherein all percentages by weight are based on the total weight of the cosmetic composition.

In yet further embodiments, a method is provided for improving smoothness, frizz-control, and alignment of hair comprising:
applying a hair treatment composition, the hair treatment composition comprising:
   about 0.1 to about 8 wt. %, preferably about 0.1 to about 3 wt. %, more preferably about 0.1 to about 0.3 wt. % of xylan or derivatives thereof;
   about 0.2 to about 23 wt. %, preferably about 0.2 to about 8 wt. %, more preferably about 0.2 to about 1 wt. % of gluconic acid,
      wherein a weight fraction of the total amount of xylan or derivatives thereof to the total amount of gluconic acid is greater than 0.2 to less than 1, preferably greater than 0.2 and less than 0.8, preferably about 0.25 to about 0.75, and more preferably about 0.3 to about 0.7, and even more preferably about 0.35 to about 0.6,
   about 2 to about 45 wt. %, preferably about 2.5 to about 25 wt. %, more preferably about 3 to about 5 wt. %, of sorbitol; and
   water, wherein all percentages by weight are based on the total weight of the cosmetic composition
rubbing the hair treatment composition into hair.

EXAMPLES

The following non-limiting examples are provided primarily for the purposes of elucidating the benefits and properties achieved by aspects of the invention.

Example 1

A hair composition (Exemplary Formulation A) was prepared containing the components and amounts listed in Table 1, provided below. Exemplary Formulation A was in the form of an emulsion.

TABLE 1

| | US INCI NAME | Exemplary Formulation A |
|---|---|---|
| (a) Xylan | XYLAN | 0.2 |
| (b) Gluconic acid | GLUCONIC ACID | 0.5 |
| (c) Sorbitol | HYDROGENATED STARCH HYDROLYSATE | 3.5 |
| (e) Silicone | AMODIMETHICONE | 1.71 |
| (f) Cationic Surfactant | CETRIMONIUM CHLORIDE | 0.03 |
| | BEHENTRIMONIUM CHLORIDE | 2.528 |
| (g) Fatty Compound | CETEARYL ALCOHOL | 6.5 |
| Miscellaneous | Nonionic Surfactant, Preservatives, pH adjuster, Water-soluble solvent, Fragrance, etc. | ≤3 |
| (d) Water | WATER | 82.756 |

Example 2

Exemplary Composition A (as provided in Example 1) was evaluated to assess the conditioning and styling effects of Exemplary Compositions A and B on hair swatches. Comparative Composition C and D include xylan, gluconic acid, and sorbitol, but in amounts outside the preferred ranges disclosed herein. The xylan, gluconic acid, and sorbitol were the only components in Exemplary Compositions A and B and Comparative C and D providing a conditioning effect. Comparative Composition E was prepared similar to Exemplary Compositions A and B and Comparative Composition C and D, but Comparative Composition E did not contain xylan. Commercial Benchmark F was a commercially available conditioning product. The formulation for Commercial Benchmark F is provided below.

TABLE 2

| | US INCI NAME | Commercial Benchmark F |
|---|---|---|
| Cationic surfactant | BEHENTRIMONIUM CHLORIDE AND/OR CETRIMONIUM CHLORIDE | 2.5 |
| Fatty Compound (non oil) | CETEARYL ALCOHOL | 6.5 |
| Siliccone | AMODIMETHICONE | 1.7 |
| Miscellaneous | Nonionic Surfactant, Plant or vegetable oils, Plant/fruit extracts, Preservatives, pH adjuster, Water-soluble solvent, Fragrance, etc. | ≤3 |
| | WATER | 87 |
| | WATER/AQUA | Qs 100 |

Exemplary Compositions A and B, Comparative Composition C-E, and Commercial Benchmark F were applied separately to hair swatches to determine the effect of such compositions. Each of the hair swatches was washed with shampoo before treatment with the foregoing compositions. After shampooing, the wet hair swatches were treated with approximately 0.15 grams of the foregoing compositions per gram of swatch, which was allowed to remain on the hair swatches for about 1 minutes. The hair swatches were subsequently rinsed off, blown dried, and subsequently combed twice before being evaluated. The hair swatches were evaluated after the application, drying and combing of the hair swatches (evaluation at time T0).

Table 3, presented below, provides a summary of the components providing a conditioning effect and a summary of the evaluation of the hair swatches after combing (T0).

TABLE 3

| | Exemplary Composition A | Exemplary Composition B | Comparative Composition C | Comparative Composition D | Comparative Composition E | Commercial Benchmark F |
|---|---|---|---|---|---|---|
| Active Components | (0.2 wt. % of Xylan, 0.5 wt. % of Gluconic Acid, & 3.5 wt. % of Sorbitol) | (0.2 wt. % of Xylan, 0.25 wt. % of Gluconic Acid, & 3.5 wt. % of Sorbitol) | (0.5 wt. % of Xylan, 0.5 wt. % of Gluconic Acid, & 3.5 wt. % of Sorbitol) | (0.2 wt. % of Xylan, 1 wt.% of Gluconic Acid, & 3.5 wt. % of Sorbitol) | (0.5 wt. % of Gluconic Acid & 5 wt. % of Sorbitol) | (Conditioning acgents: aminosilicone and cationic surfactants, such as behen-trimonium chloride and cetrimonium chloride) |

TABLE 3-continued

|  | Exemplary Composition A | Exemplary Composition B | Comparative Composition C | Comparative Composition D | Comparative Composition E | Commercial Benchmark F |
|---|---|---|---|---|---|---|
| Weight fraction of Xylan to Gluconic Acid | 0.4 | 0.8 | 1 | 0.2 | — | — |
| Description of Hair Swatches | Smoother, well aligned, shaped well, close ends | Smooth, aligned, very slightly shaped, open ends | Less smooth, feel fibers, slightly shaped, open ends | Very smooth, not shaped, not well aligned, more volume | Smoother, aligned, slightly shaped, open ends | Smooth, open ends, slight volume |

The hair swatches were evaluated for a second time after remaining in a humidity chamber at 23° C. and 80% humidity (time, T72 hours). As part of the evaluations, the smoothness, the alignment, the shape, and the ends of the hair swatches were assessed on a scale ranging from 1 to 5. A value of 5 was assigned to hair swatches exhibiting the best evaluated property and a value of 1 assigned to hair swatches exhibiting the worst evaluated property.

Table 4, provided below, includes a summary of the evaluation of the hair swatches. Because the evaluated attributes did not change significantly between the first evaluation and the second evaluation, only one value is provided for each evaluated attributes.

TABLE 4

|  | Exemplary Composition A | Exemplary Composition B | Comparative Composition C | Comparative Composition D | Comparative Composition E | Commercial Benchmark F |
|---|---|---|---|---|---|---|
| Description of Hair Swatches | Smoother, aligned, shaped well, slightly open ends. | Smooth, can feel slight fibers, open ends. | Less smooth, feel fibers, slightly shaped, open ends. | Smooth, not shaped, not well aligned, more volume. | Smooth, can feel slight fibers, open ends and can feel ends, slightly shaped. | Smooth, can feel slight fibers, open ends and can feel ends. |
| Smoothness | 5 | 3 | 2 | 3 | 3 | 3 |
| Alignment | 5 | 3 | 3 | 2 | 3 | 2 |
| Shape | 4 | 2 | 3 | 2 | 3 | 2 |
| Ends | 5 | 2 | 3 | 2 | 3 | 2 |

As shown in Tables 3 and 4, Exemplary Compositions A and B and Comparative Compositions C and D provided better smoothness, hair alignment, shape, and closure of the ends than Comparative Composition E and Commercial Benchmark F. However, it is clear from Table 4, that the ratio of the amounts of xylan, gluconic acid, and sorbitol, especially, the ratio of the amounts of xylan to gluconic acid, affected the level of smoothness, frizz control, hair alignment exhibited by the hair swatches. With the weight fraction of xylan to gluconic acid of 0.4, Exemplary Composition A provided the best results with respect to smoothness, alignment, shape, and ends at both time points T0 and T72.

Example 3

Exemplary Composition A and Commercial Benchmark F were each applied to hair on half of the head of 6 individuals. Specifically, each of the individual's hair was rinsed for about 30 seconds, and subsequently applied with 10 grams of Exemplary Composition A and Commercial Benchmark F. The foregoing compositions were rinsed from the hair of each individual, and the hair was blow dried and combed each individual self-assessed their hair.

FIG. 1 provides images of each of the individuals' hair after blow drying and combing. The left side of each of the individuals' head hair received Exemplary Composition A and the right side of each of the individuals' head hair received Commercial Benchmark F. Table 5, shown below, provides a summary of the comments from a self-assessment by the individuals' regarding the attributes of the portion of their hair receiving Exemplary Composition A as compared to the portion of their hair receiving Commercial Benchmark F.

TABLE 5

Exemplary Composition A vs. Commercial Benchmark F

| No. | CP/Hair type/Treatment | Evaluation - Stylish | Evaluation-Model |
|---|---|---|---|
| 1 | CP 1/Medium-Fine to avg./Color treated & highlights | Preferred Exemplary Composition B for volume, shape natural look, shine, smoothness | |
| 2 | CP 1/Medium-Fine to avg./Color treated | Preferred Exemplary Composition B for volume, shape and shine, smooth, not frizzy | |
| 3 | CP 3/Long-avg./Color treated | Preferred Exemplary Composition B for volume, shine, shape, discipline | |
| 4 | CP 2/Short to med-fine/Color treated | Preferred Exemplary Composition B for fullness, shape and styling property, Discipline | |

TABLE 5-continued

Exemplary Composition A vs. Commercial Benchmark F

| No. | CP/Hair type/Treatment | Evaluation - Stylish | Evaluation-Model |
|---|---|---|---|
| 5 | CP 3/Long-avg./Color treated | Preferred Commercial Benchmark F for shape and looks | No preference- in parity |
| 6 | CP 5/Med.-avg./Color treated & highlights | Preferred Exemplary Composition B for shape - coily, smoothness and softer curls | |

Based on the comments from the self-assessment, about 83% of the individuals preferred Exemplary Composition A as compared to Commercial Benchmark F. In particular, the six individuals generally stated that Exemplary Composition A provided better hair shape and hair volume. In addition, several individuals indicated that Exemplary Composition A provided better hair discipline, shine, and smoothness relative to Commercial Benchmark F.

Example 4

The elastic modulus of Exemplary Composition A was assessed on hair swatches in comparison to Commercial Benchmark F and a Control. Exemplary Composition A and Commercial Benchmark F were used as rinse out conditioners on the hair swatches after shampooing the swatches (using a traditional shampoo). The Control was distilled water.

Figure 2:
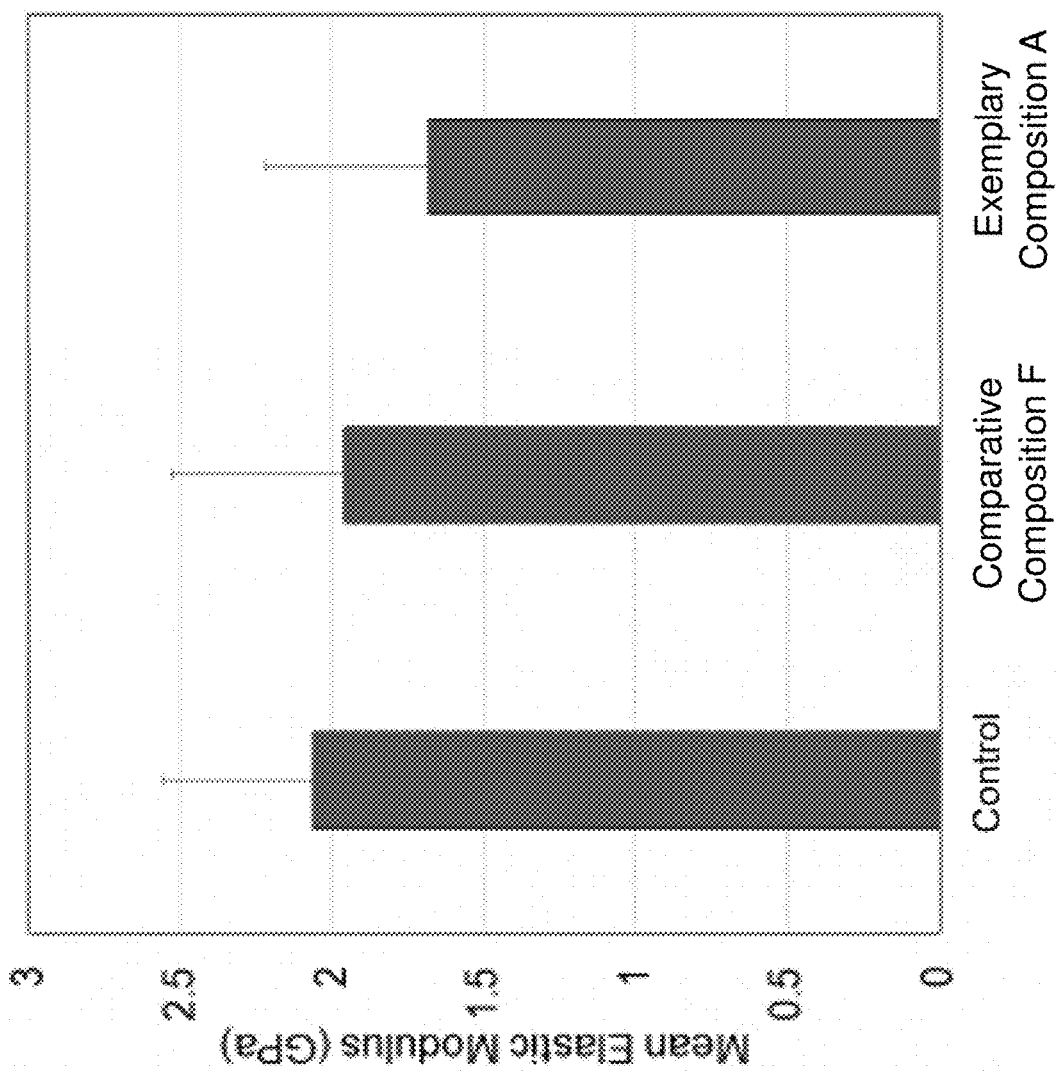
FIG. 2 is a graph comparing the elastic modulus of a hair treatment composition in accordance with aspects of the disclosure to a comparative example and a control.

The elastic modulus of Exemplary Composition A, Commercial Benchmark F, and the Control are shown in the FIG. 2. Exemplary Composition A had a lower elastic modulus than Commercial Benchmark F, and the Control. Stiffer materials have a higher elastic modulus. It was found that the deposition of the xylan-gluconic acid complex of Exemplary Composition A reduced the elastic modulus of hair, thereby making the hair less stiff.

Example 5

Figure 3A:
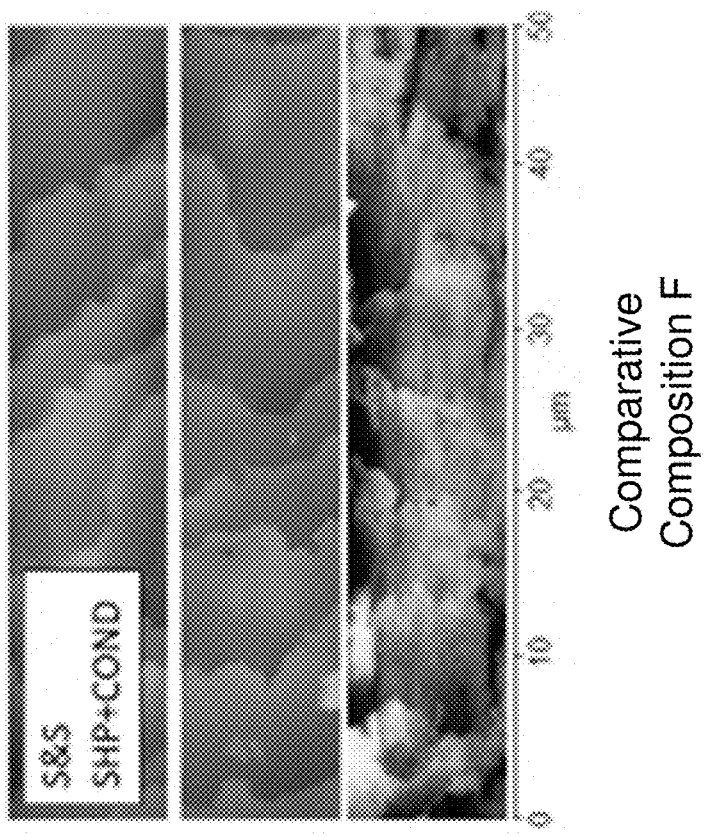
FIGS. 3A and 3B include images of the surface of the hair after application and drying of the hair treatment composition, the comparative example, and the control of FIG. 2.
Figure 3B:
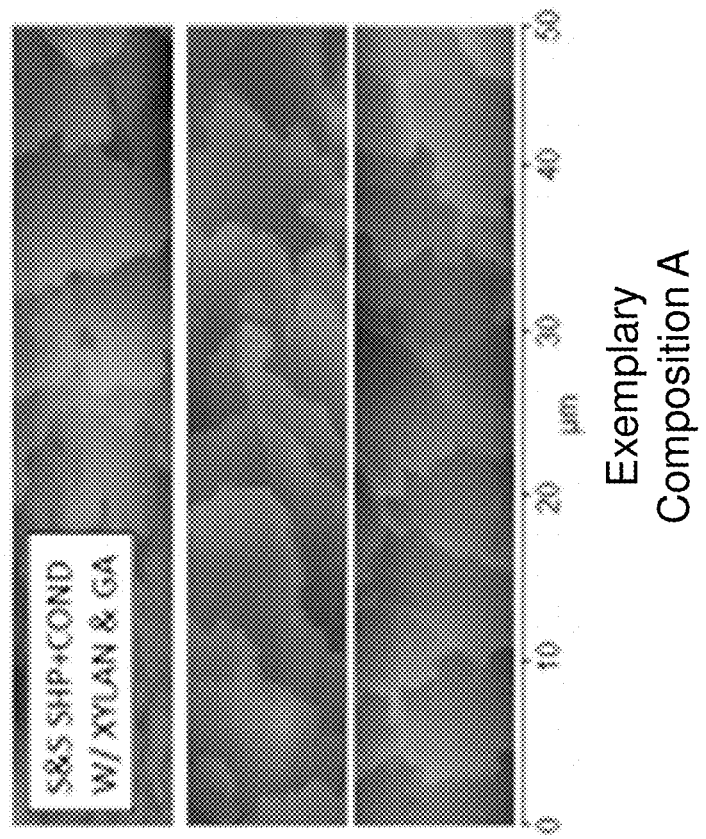

Approximately 0.15 grams per gram of hair substrate of each of Exemplary Composition A, Commercial Benchmark F, and the Control were applied to hair substrates. Each of the foregoing compositions was allowed to dry for about 72 hours at about 23° C. and under standard humidity. The surface of the hair swatches were subsequently assessed using atomic force microscopy AFM device. Images of the surface of the hair after drying of the foregoing compositions are shown in FIGS. 3A and 3B. The AFM results show that Exemplary Composition A provides a complex in the form of a very thin film on the hair cuticles, hence providing frizz control, smoothness, alignment, and hold and style to the hair.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. The hair treatment composition comprising:
   (a) about 0.1 to about 1 wt. % of xylan;
   (b) about 0.2 to about 2 wt. % of gluconic acid; and wherein the weight fraction of the total amount of xylan to the total amount of gluconic acid is from about 0.35 to about 0.6;
   (c) about 3 to about 5 wt. % of sorbitol (d) water (e) about 1% to about 10 wt. % of amino functionalized silicone wherein the amino functionalized silicone is chosen from amodimethicone, bis-hydroxy/methoxy amodimethicones, bis-cetearyl amodimethicone, bis(C 13-15 alkoxy) PG amodimethicones, aminopropyl phenyl trimethicones, aminopropyl dimethicones, bis-amino PEG/PPG-41/3 aminoethyl PG-propyl dimethicones and caprylyl methicones and mixtures there of (f) about 0.1% to about 10 wt. % of cationic surfactant, wherein the cationic surfactant is chosen from behenalkonium chloride, benzethonium chloride, cetylpyridinium chloride, behentrimonium chloride, lauralkonium chloride, cetalkonium chloride, cetrimonium bromide, cetrimonium chloride, chlorallyimethenamine chloride, distearyldimonium chloride, dodecyl dimethyl ethylbenzyl ammonium chloride, Quaternium-22, Quaternium-26, Quaternium-18 hectorite, tallow alkonium chloride, dimethyl dioctadecylammoniumbentonite, stearalkonium chloride, myristalkonium chloride, laurtrimonium chloride, methylbenzethonium chloride, myrtrimonium bromide, oleyltrimonium chloride, polyquaternium-1, stearalkonium bentonite, stearalkoniumhectonite, tallowtrimonium chloride, hexadecyltrimethyl ammonium bromide, and a mixture thereof (g) about 2% to about 20 wt. % of fatty alcohols the fatty alcohols are chosen from decyl alcohol, undecyl alcohol, dodecyl alcohol, myristyl alcohol, cetearyl! alcohol, cetyl alcohol, stearyl alcohol, isostearyl alcohol, isocetyl alcohol, behenyl alcohol, linalool, oleylalcohol, cis-4-t-butylyclohexanol, isotridecyl alcohol, myricyl alcohol, and a mixture thereof
   wherein all percentages by weight are based on the total weight of the hair treatment composition.

2. The hair treatment composition of claim 1 further comprising one or more cationic polymers.

3. The hair treatment composition of claim 2, wherein the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

4. The hair treatment composition of claim 1 being a rinse-off conditioner.

5. A method for improving smoothness, and alignment of hair comprising:
   (a) applying the hair treatment composition of claim 1 to the hair; and
   (b) rubbing the hair treatment composition into the hair.

6. The method of claim 5 further comprising rinsing the hair treatment composition from the hair.

* * * * *